(12) United States Patent
O'Neill

(10) Patent No.: US 12,133,812 B2
(45) Date of Patent: Nov. 5, 2024

(54) FEMALE URINARY INCONTINENCE MANAGEMENT SYSTEM

(71) Applicant: Suzanne Mary O'Neill, Medford, MA (US)

(72) Inventor: Suzanne Mary O'Neill, Medford, MA (US)

( * ) Notice: Subject to any disclaimer, the term of this patent is extended or adjusted under 35 U.S.C. 154(b) by 444 days.

(21) Appl. No.: 17/479,075

(22) Filed: Sep. 20, 2021

(65) Prior Publication Data

US 2022/0088380 A1  Mar. 24, 2022

Related U.S. Application Data

(60) Provisional application No. 63/080,220, filed on Sep. 18, 2020.

(51) Int. Cl.
*A61F 5/455* (2006.01)

(52) U.S. Cl.
CPC ..................... *A61F 5/455* (2013.01)

(58) Field of Classification Search
CPC ............... A61F 5/455; A61H 19/34
USPC ........................................... 604/38
See application file for complete search history.

(56) References Cited

U.S. PATENT DOCUMENTS

| | | | |
|---|---|---|---|
| 3,672,371 A | 6/1972 | Roeder | |
| 4,568,339 A | 2/1986 | Steer | |
| 4,781,713 A | 11/1988 | Welch et al. | |
| 5,336,208 A * | 8/1994 | Rosenbluth | A61F 5/48 604/387 |
| 5,417,226 A | 5/1995 | Juma | |
| 5,571,118 A * | 11/1996 | Boutos | A61H 19/30 607/143 |
| 5,895,349 A | 4/1999 | Tihon | |
| 6,179,769 B1 | 1/2001 | Ishikawa et al. | |
| 6,224,541 B1 * | 5/2001 | Thompson | A61H 19/34 600/38 |
| 6,246,915 B1 * | 6/2001 | Boutos | A61N 1/0512 607/39 |
| 6,941,171 B2 | 9/2005 | Mann et al. | |
| 6,964,643 B2 | 11/2005 | Hovland et al. | |
| 7,621,899 B2 | 11/2009 | Fujikawa et al. | |
| 7,855,653 B2 | 12/2010 | Rondoni et al. | |
| 7,931,634 B2 | 4/2011 | Swiecicki et al. | |
| 8,684,008 B2 | 4/2014 | St. Anne | |
| 8,918,175 B2 | 12/2014 | Nelson et al. | |
| 9,623,231 B2 | 4/2017 | Kolb et al. | |
| 10,322,282 B2 | 6/2019 | Wei et al. | |
| 2002/0120219 A1 * | 8/2002 | Hovland | A61H 19/34 601/72 |
| 2011/0162661 A1 * | 7/2011 | St. Anne | A61F 13/47209 128/885 |

(Continued)

*Primary Examiner* — Andrew J Mensh
(74) *Attorney, Agent, or Firm* — Daniel N. Smith

(57) ABSTRACT

The invention is a viscoelastic protuberance anchored through the back of a pad and projecting from the absorbing side of the top third of the pad. The shape and length of the protuberance is ideal for interlabial positioning with crucial clitoral contact. This contact is secured by a taut under garment. Lower pelvic or upper thigh movements of the user introduce a mild friction between the protuberance and the users clitoris which serves to trigger mild sexual arousal. A reflexive neurological pathway is then activated which diminishes the urge to urinate—a female physiological law.

20 Claims, 16 Drawing Sheets

(56) References Cited

U.S. PATENT DOCUMENTS

| | | | |
|---|---|---|---|
| 2013/0184778 A1* | 7/2013 | St.Anne | A61F 15/002 607/2 |
| 2013/0317467 A1 | 11/2013 | Campbell | |
| 2014/0221885 A1* | 8/2014 | Fleschere | A41B 9/04 601/46 |
| 2015/0119636 A1* | 4/2015 | Yenko | A61H 23/0254 600/38 |
| 2015/0352357 A1* | 12/2015 | Wei | A61N 1/0456 604/385.03 |
| 2020/0001080 A1 | 1/2020 | Naitoh | |

* cited by examiner

FEMALE URINARY INCONTINENCE MANAGEMENT SYSTEM

CROSS-REFERENCE TO RELATED APPLICATION

This application claims the benefit of priority of U.S. Pat. No. 4,337,772A, application granted Jul. 6, 1982, the contents of which are herein incorporated by reference.

BACKGROUND OF THE INVENTION

Humane men and women, of considerable talent, have long sought to solve or ameliorate the problem of female urinary incontinence. Only the Sanitary Napkin with garment attachment adhesive (U.S. Pat. No. 4,337,772A) has offered a tentative solution. The actual discomfort of wearing a urine-soaked pad, for any length of time, remains, as does the possibility of causing "adult diaper rash" with continuous daily use. Still the Sanitary Napkin has done a great deal to restore quality of life to the aging. As an essential component in the Female Urinary Incontinence Management System (FUIMS) disclosed in this patent, the pad attains a maximum level of daily utility, and comfort, potentially offering relief to millions.

Previous patents disclose an alarming array of "solutions": electrodes (US20200001080), (U.S. Ser. No. 10/322, 282), (U.S. Pat. No. 9,623,231), electrodes implanted within the body (U.S. Pat. No. 6,941,171). One uses genital suction or vacuum: U.S. Pat. No. 6,964,643. An intrusive device is inserted into the urethra itself: U.S. Pat. No. 5,417,226. These talented men and women have used creativity and mental energy on behalf of women everywhere, who suffer diminishment of life's joys through incontinence. We cannot doubt the beneficence of their motivation.

This patent is the first to use one anatomical female feature, and one female physiological fact, to create a Female Incontinence Management Device (FIMD) that when united with an adhesive backed pad, forms a comfortable and effective Female Urinary Incontinence Management System (FUNIS).

Neither electric, intrusive or pharmaceutical in its nature, the disclosed FUNIS requires only mild frictional stimulation of the user's clitoris to ameliorate the urge to urinate.

The anatomical feature I will call the clitoral-urethral meatus space (C-UMS). Between the Labia Majora and the Labia Minora there exists a small flesh platform, if you will: the C-UMS. The distance from the base of the clitoris to the urethral meatus, has been calculated to be on average, ¾ of an inch, by Dr. Marie Bonaparte, a pioneer in sex research. This average measurement is valuable in establishing a maximum length for a device to be placed within the user's C-UMS, with its crucial access to the clitoris.

The important physiological fact is this: Stimulation of the clitoris causes reflexive contraction of the bulbocavernosus and the ischiocavernosus muscles. This contraction serves to close both the external and internal urethral sphincters, so coitus remains uninterrupted. Stimulation of the dominant female arousal system is designed to block the urge to urinate—a physiological fact.

By attaching a small protuberance of viscoelastic foam to a base and passing this device through a sanitary napkin at an appropriate spot, one is able to successfully introduce a benign trigger to the female arousal system. Once the protuberance is manipulated to make clitoral contact and the pad is adhered to a taut undergarment, conscious clitoral stimulation can be achieved, blocking the urge to urinate. Discrete muscle movement, even crossing one's legs can induce the mild friction necessary between the protuberance and the user's clitoris to induce a sensation of arousal. With the arousal system triggered, one can successfully suppress/manage the urge to urinate, until one can conveniently void. Leakage onto the pad, though not absent, will be minimal.

SUMMARY OF THE INVENTION

The FIMD (Female Incontinence Management Device) is a foam protuberance, of varying shapes and sizes. Both soft and pliable, it is virtually non-abrasive. Said protuberance is attached to a circular base, to form the device.

Said device is pulled through a pad at a particular point, allowing the protuberance to fully project from the absorbing side of the pad. The abraded side of the circular base is then pressed firmly against the adhesive side, to create a seal.

The protuberance is positioned in the C-UMS (Clitoral Urethral Meatus Space) and makes contact with the user's clitoris. It is crucial that said contact is achieved and maintained. To this purpose, a tight pair of underpants is worn. To avoid discomfort, a thong may be worn backwards, passing the band firmly over the contact area. This adds another layer of stabilization.

No electrodes, pharmaceuticals, surgical implants, catheters, or adhesives are needed. The user self-stimulates. Modest lower pelvic, upper thigh movements, even crossing one's legs is enough to cause mild friction between the well positioned protuberance, and the user's clitoris. The sexual arousal system is triggered; the urge to urinate is blocked.

The device is reusable and can be worn daily. One simply unglues the base from the adhesive side of the pad, and carefully eases the expanded protuberance back out. The released protuberance is then washed with dish detergent, rinsed, and squeezed with a clean towel, to remove excess moisture from the expanded foam. Set upright on its base, perhaps resting in a provided tin, it is sprayed with Isopropyl alcohol and allowed to dry. Shrinking to its original size overnight, the protuberance is ready the following morning for insertion into a fresh pad.

As effective as it is simple, the device can contain a stiffener, embedded in the protuberance to a desired depth. Some may prefer the enhanced rigidity of this adaptation.

BRIEF DESCRIPTION OF THE DRAWINGS

FIG. 48 is a pad back view, further showing essential markings.

FIG. 78 is a back pad view showing neoprene base adhesion.

FIG. 88 is a bell shaped FIMD, pad back, showing an internal stiffener.

DETAILED DESCRIPTION OF THE INVENTION

This patent describes the fabrication of a female incontinence management device (FIMD) with one adaptation of said device: implanting a nylon stiffener into a viscoelastic foam protuberance. Two different bases constitute two distinct embodiments: a neoprene disc base, and a single unit synthetic base. The FIMD is placed, with specifications, into a commercial pad (U.S. Pat. No. 4,337,772A). The union of the FIMD with the pad constitutes the Female Urinary Incontinence Management System (FUIMS). The use of said system is most appropriate for age related, urge (non-stress) urinary incontinence that is moderate to severe.

The user of said system adheres the pad containing the FIMD, with either base, onto the inside crotch area of a taut pair of underwear, protuberance pointing upwards. Raising the under garment, said protuberance is placed between the labia majora, and the labia minors, within the user's C-UMS, making the essential contact with the clitoris. The taut under garment is completely raised, carefully maintaining said position. A thong, worn backwards, could be added to further stabilize the crucial clitoral contact.

As the FUIMS is habitually worn, changing the nerve tracts in, at least, a semi-permanent way, the exact initial position of protuberance i.e., clitoral contact, may no longer be necessary. The FUIMS, with its device protuberance, could be placed within the user's C-UMS near the clitoris, to remain effective. When beginning the use of the FUIMS, however, protuberance contact with the clitoris is crucial to train the body.

The wearer of said system, conscious of the beginning of an urge to urinate, discretely flexes upper thigh, lower buttocks, or pelvic floor muscles, to trigger a mild friction between the protuberance and the user's clitoris. Said friction immediately diminishes the urge to urinate, by causing a mild auto erotic response. One is able, within a short period of time, to learn how to manage the unwanted impulse. Because the stimulation is intermittent, and of short duration, it is unlikely to cause the clitoris to become engorged.

This system is designed to buy time, in relative comfort, until the user is able to void. The pad saturation, though not absent, is light, adding both a measure of comfort and of security.

Figure 9:
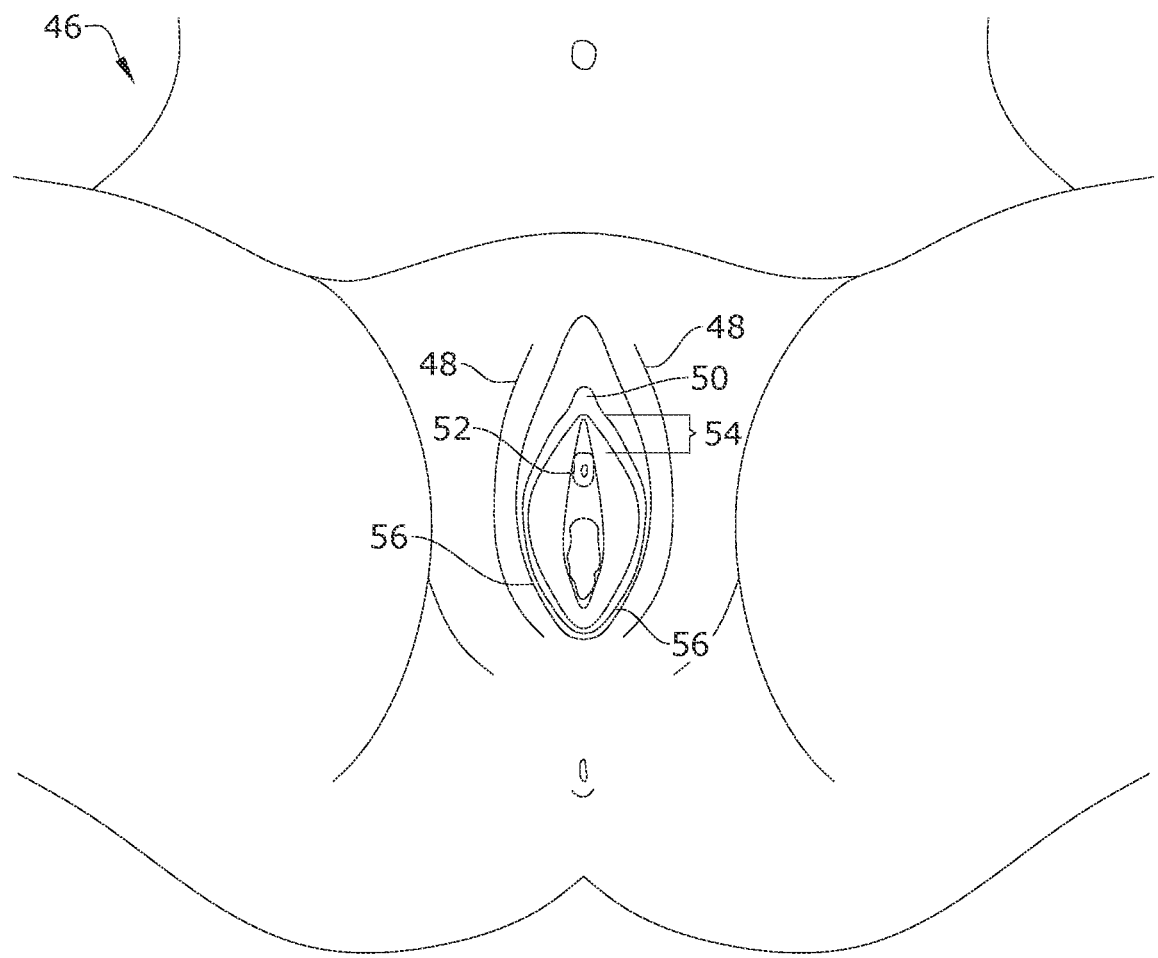
FIG. 9 is a diagram of female external genitalia.

The anatomy of the user is shown in FIG. 9 number 46. The viscoelastic protuberance of the FIMD nestles, when worn, between the labia majora 48 and the labia minora 56. The protuberance rests within the C-UMS 54, a space measuring on average ¾ of an inch from the base of the clitoris 50 to the urethral meatus 52, Clitoral contact with the viscoelastic protuberance, placed within the C-UMS, is essential.

Figure 4A:
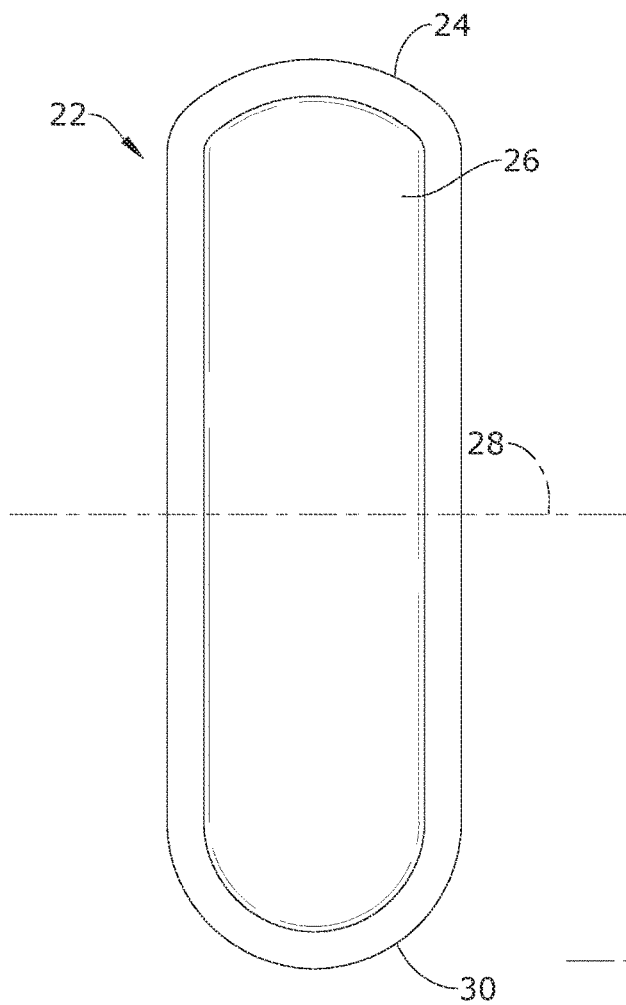
FIG. 4A is pad front view, showing a medial line, and a top end and a bottom end of the pad.
Figure 4B:
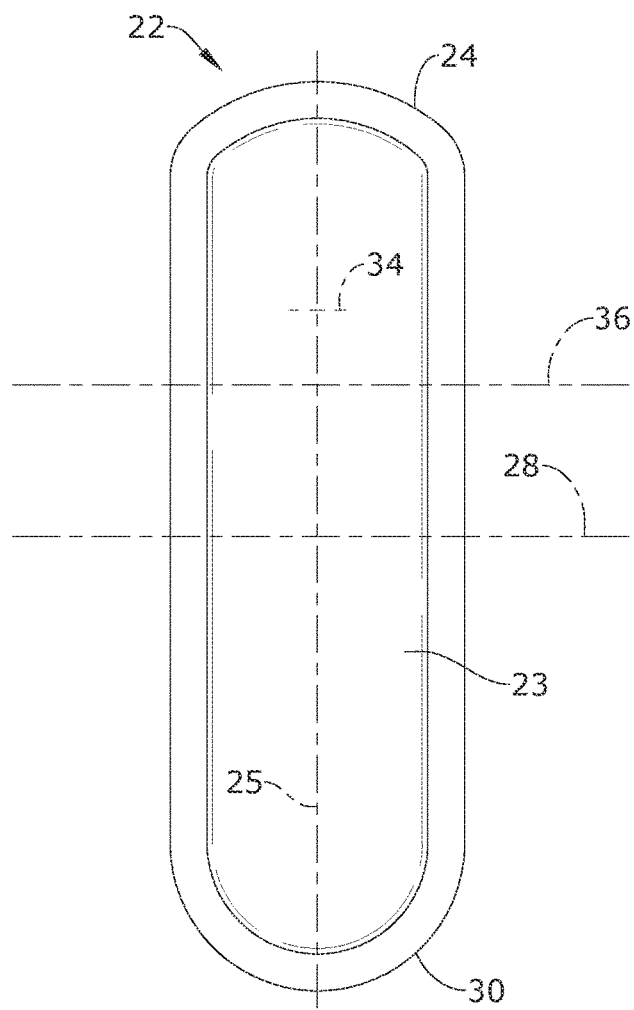

The Female Urinary Incontinence Management System, (FUIMS), is the union of the Female Incontinence Management Device, (FIMD), with an absorbing matrix, a pad. FIGS. 4A and 4B detail the sections of the pad that apply to this invention.

22 is the pad itself. 24 is the top end of the pad. 30 is the bottom end of the pad. 26 is the front, absorbing side of the pad. 23 is the back, adhesive side of the pad. 28 is the medial line of the pad. 25 is the medial lengthwise line on 23 the back of the pad. 36 is the line marking the top ⅓ of the pad, 34 is the ideal spot to cut an opening.

Figure 12:
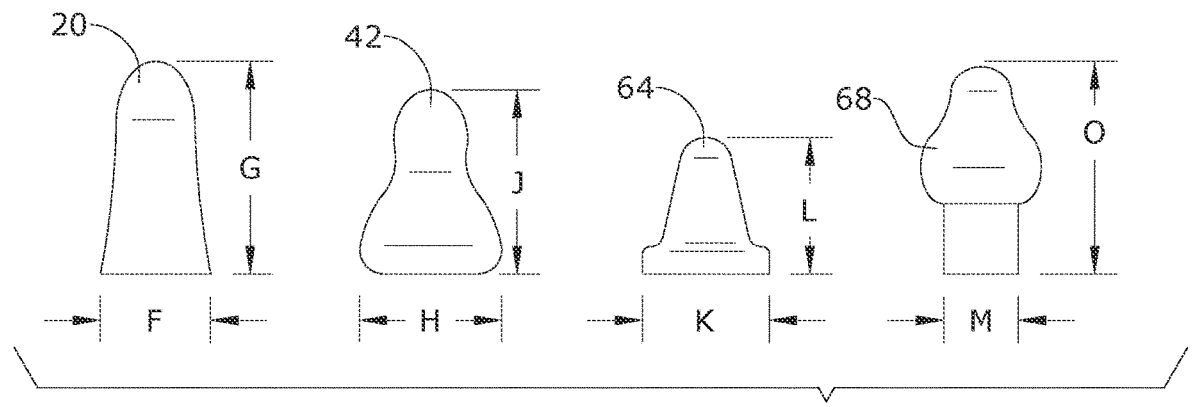
FIG. 12 is an assortment of 4 viscoelastic protuberances, showing length and width.

Pliability, shape, size, and firmness are the features to consider in the FIMD's viscoelastic protuberance. FIG. 12 shows a range of commercially available viscoelastic protuberances with appropriate features, or with the possibility of adapting the protuberance for a necessary feature. 20 is a PVC free conical viscoelastic protuberance, measuring ½ of an inch (F), by 1³⁄₁₆ of an inch (G). Bell shaped protuberance 42 measures ⅝ of an inch (H) by ¹⁵⁄₁₆ of an inch (J). Protuberance 64 measures ¾ of an inch (K) by ⅞ of an inch (L). Finally, 68 measures ⅜ of an inch (M) by 1¼ inches (0). These variable lengths, from 1¼ inches to ⅞ of an inch, and the unique shapes, suggest the possibility of maximizing user comfort.

Figure 13:
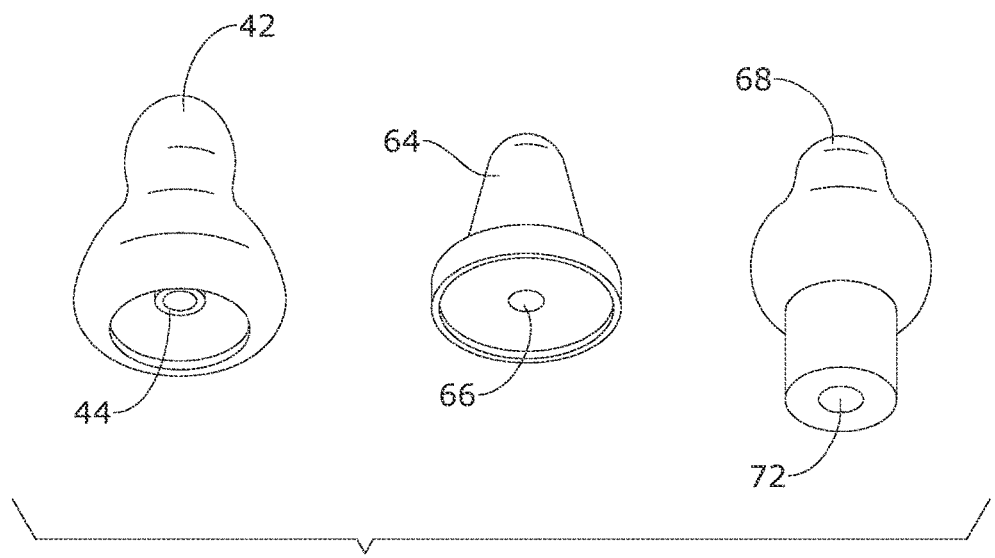
FIG. 13 is a view of distinct features of 3 viscoelastic protuberances.
Figure 14A:
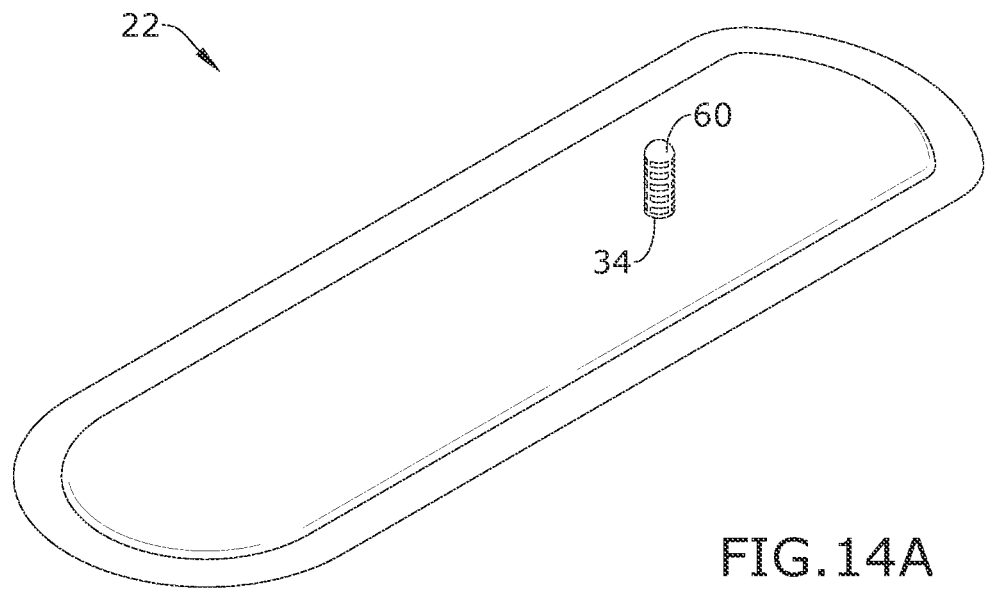
FIG. 14A is a front pad view with the one piece base inserted.
Figure 14B:
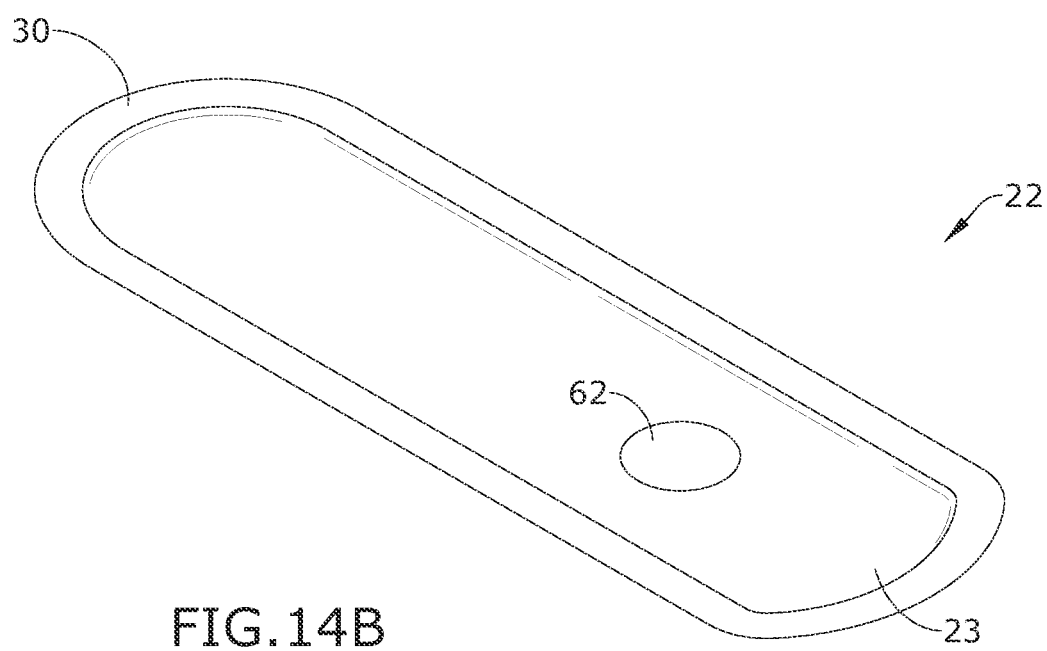
FIG. 14B is a back pad view with the one piece base inserted.

FIG. 13 shows the unique features of 42, 64, and 68. A pliable viscoelastic protuberance, alone, once it has absorbed fluid and/or secretions, is unsuitable as a dependable source of clitoral stimulation, once positioned; a stiffener must be introduced. In the case of 42 a stiffener is already integrated 44. Both 64 and 68 have factory made openings, 66 and 72 respectively. These openings allow for the insertion of a stiffener. Only 20 must be adapted to contain the essential stiffener.

Figure 10:
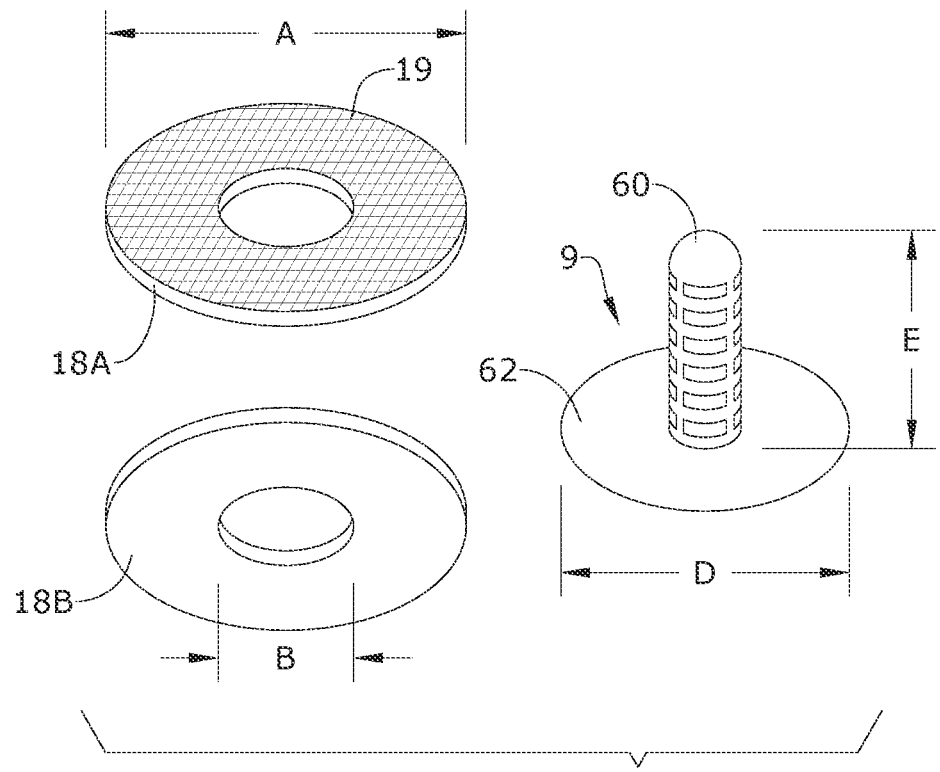
FIG. 10 are views of the two types of bases: the washer base and the one-piece synthetic base.

FIG. 10 illustrates two types of bases used to anchor the FWD to 23 the pad back. 19 is a neoprene washer with a central opening B measuring ⅜ of an inch in diameter, A, the outer diameter of base 19, measures 1¼ inches. Side 18a is abraded to ensure a bond with the 23 the pad back; 18b remains smooth. The second base, 9, is a one-piece synthetic with a post 60 measuring ¹³⁄₁₆ of an inch (E). 62 is a slightly convex disc measuring ¾ of an inch in diameter (D).

Figure 11:
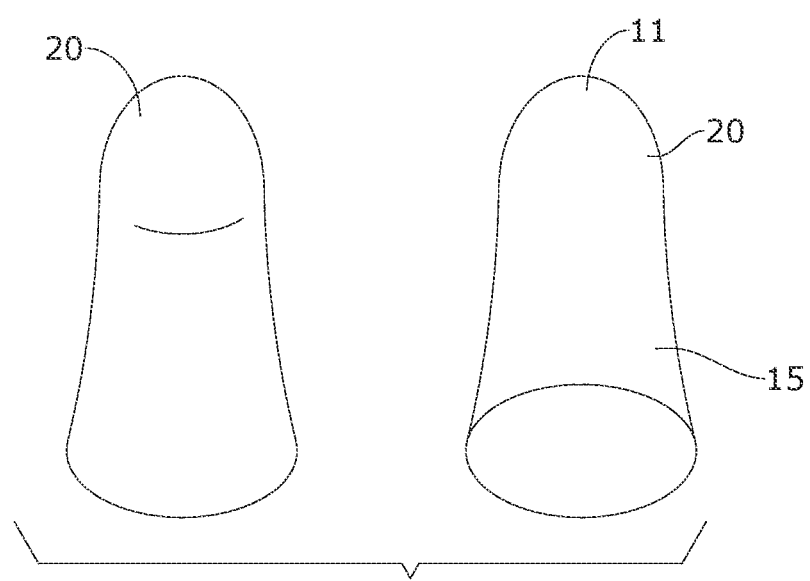
FIG. 11 is two views of a PVC free viscoelastic conical protuberance.
Figure 15:
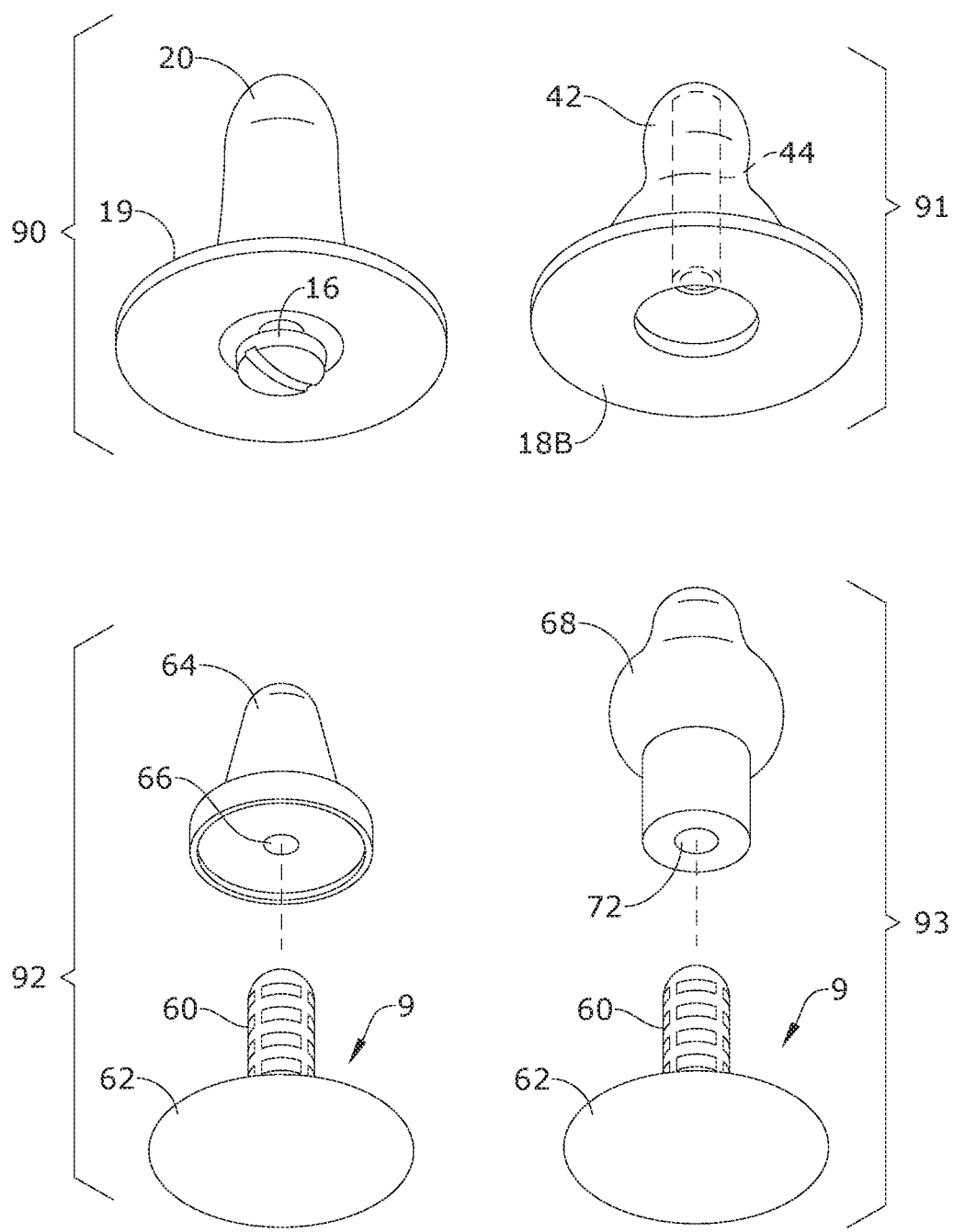
FIG. 15 is a bottom perspective view of the 4 types of FIMDs and their respective components.

Fabrication of an FIMD, with a stiffener adaptation:
Components: Cyanoacrylate bonding agent
  neoprene disc 19
  Viscoelastic foam protuberance 20: FIG. 11 having a first end (11) of lesser diameter than its second end (15).
Fabrication steps:
  1. Using 80 grit sandpaper, finely abrade one side of the neoprene disc 19. This abraded top side of the washer 18a is very important for bonding the second end of the protuberance 15 securely to the neoprene base 19 and for adhering the completed FIMD to the back of the pad 23. The abraded surface 18a will create a moisture barrier as well as serve to stabilize the FIMD when the pad is in use.
  2. On abraded side 18a of base 19 ring the center opening with 5 to 7 drops of cyanoacrylate, depending on the size of the drops,
  3. Quickly center and firmly press end 15 of protuberance 20 onto the glue droplets to create a bond. (A piece of tinfoil might be used to prevent the fabrication from bonding to the worktable) FIMDs containing protuberances 20 and 42 are fabricated in this fashion. Refer to FIGS. 15, 90 and 91.

Figure 1:
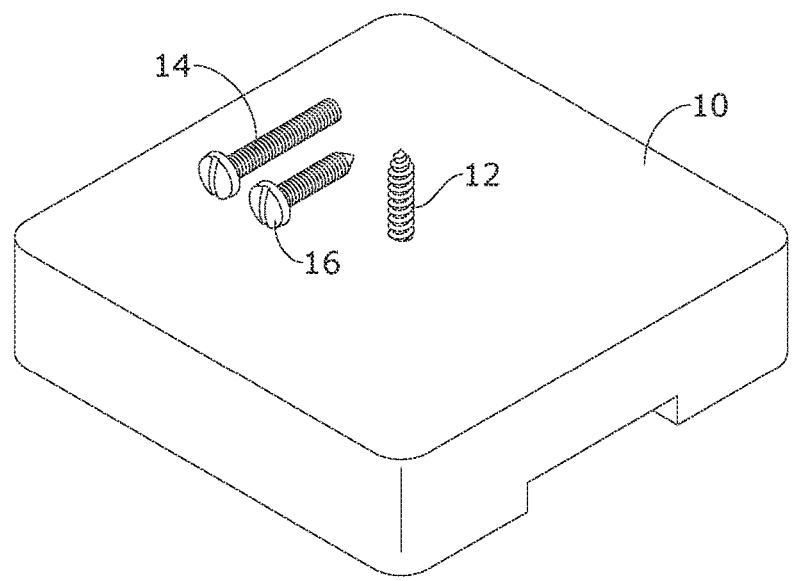
FIG. 1 is a perspective view of assembly elements for stiffener insertion into a viscoelastic protuberance.
Figure 2:
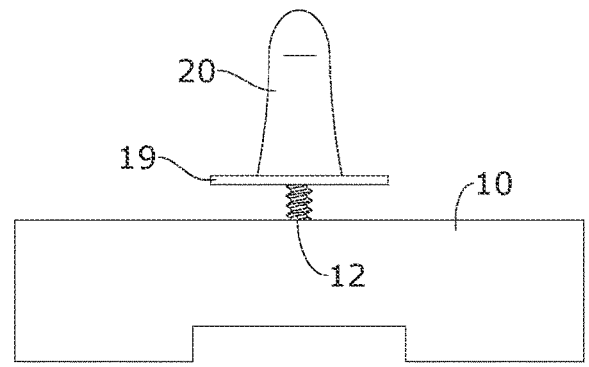
FIG. 2 is an FIMD being prepared for stiffener insertion.

Installing a stiffener to create FIMD 90: Refer to page 1/16.
  Components: FIG. 1: 10 is a small level wood block
  14 is a nylon screw, 5/32 of an inch diameter, and 1 inch long.
  12 is a metal screw slightly wider at its top point than 5/32 of an inch and long enough to project ¾ of an inch above the level wood block surface 10.
  FIG. 2 shows PVC free protuberance 20 adhered to the abraded side 18a of base 19.
  1. Screw metal screw 12 through the underside of wood block 10. Care must be taken so that metal screw 12 rests perpendicular to the wood surface 10, measuring ¾ of an inch high.
  2. FIG. 2: Accurately center protuberance 20 with its base 19 over projected metal screw 12.
  3. Firmly, but gently twist protuberance 20 onto metal screw 12 until base 19 rests flat on wood block surface 10.
  4. Release the device. An elongated opening has been fashioned.
  5. Cut nylon screw 14 to make 16: ¾ of an inch long with a pointed tip,
  6. Center and hand twist nylon screw 16 into the created opening in PVC free protuberance 20.
  7. Using a screwdriver and fairly firm pressure, screw the last ¼ inch of nylon screw 16 in meet the bottom of foam protuberance 20.

Figure 3:
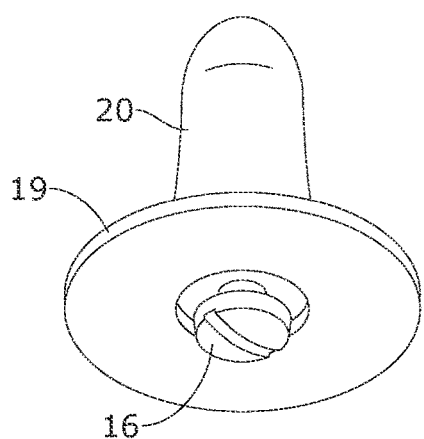
FIG. 3 is a bottom perspective view of the completed assembly.

FIG. 3 shows nylon screw 16 nearly making the ideal contact with protuberance bottom of second end 15, FIG. 11. FIMD 90 is thus fabricated.

Figure 5:
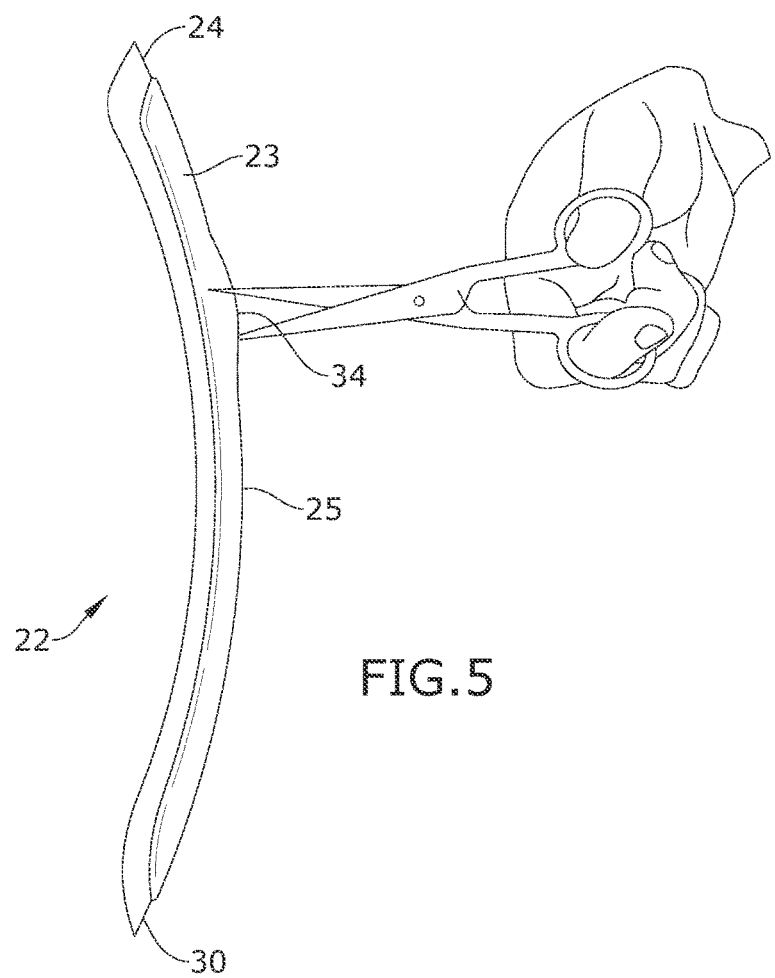
FIG. 5 is a pad side view illustrating user preparation for insertion of an FIMD.
Figure 6:
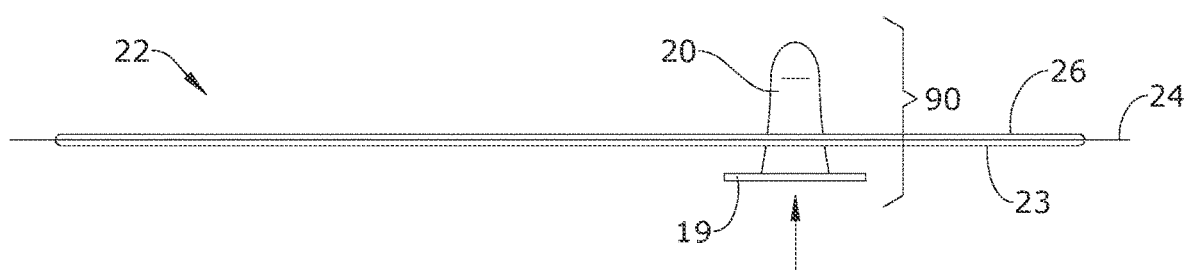
FIG. 6 is a lateral view of the FIMD partially inserted into a pad.
Figure 7A:
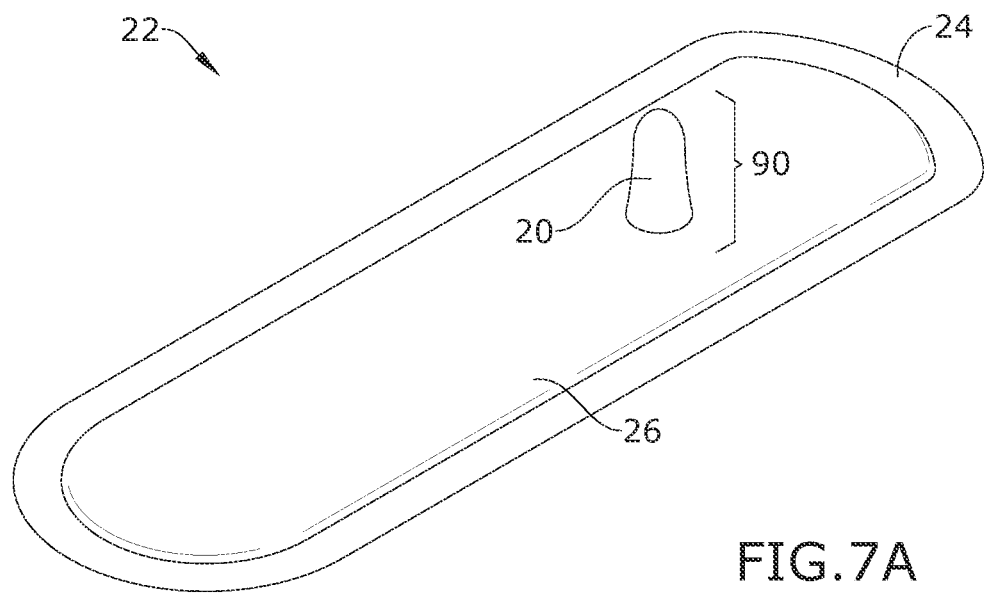
FIG. 7A is a front pad view with the FIMD inserted.
Figure 7B:
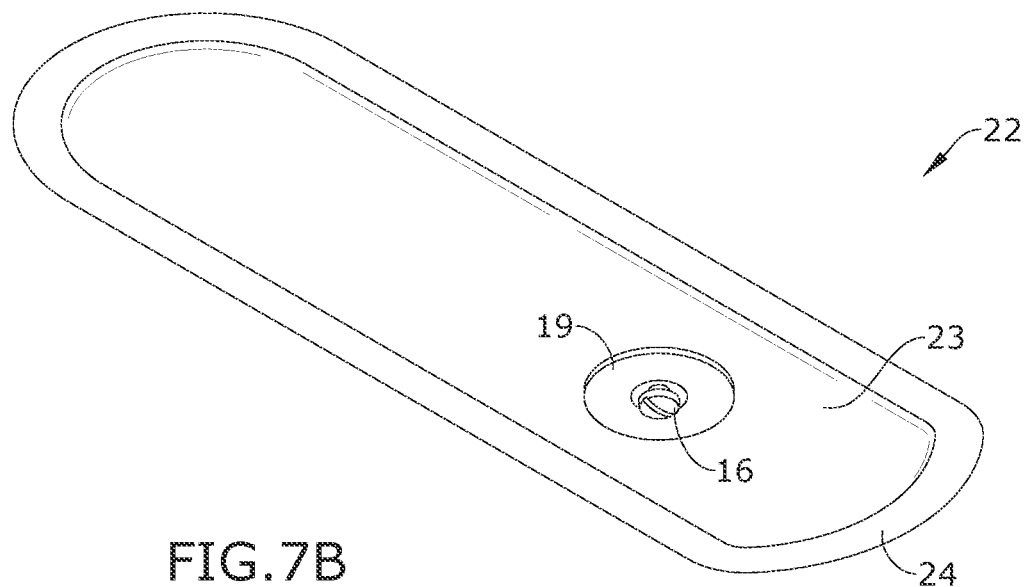

Positioning the FIMDs with the neoprene disc base 19, into a pad:
  Components: a sealed pad
  FIMD 90 or 91 (please refer to FIG. 15, page 10/16)
  a pair of scissors
  Please refer to FIGS. 5 and 6 on page 3/16:
  1. Open the sealed pad 22, and pull the protective plastic off, to reveal the top end 24 of the pad back 23.
  2. Pinch both pad sides of the pad together to create medial lengthwise fold 25.
  3. Cut a half inch opening (¼ of an inch cut on each side of the fold) at 34, the ideal opening in the top ⅓ of the pad.
  4. With a pinkie, through the back of the pad 23, slightly round out and expand the opening.
  5. Compress the first end 11 of the foam protuberance.
  6. Pass the compressed end through the opening 34 from the back side of the pad 23.
  7. Gently tease the remainder of the protuberance through, FIG. 6.
  8. FIG. 7A shows the ideal placement of FIMD 90, fully projecting from the pad front 26, in the top end of the pad 24.
  9. FIG. 7B shows pad 22 with base 19 adhered to the pad back 23 at the top end of the pad 24. Note implanted stiffener 16.

Figure 8A:
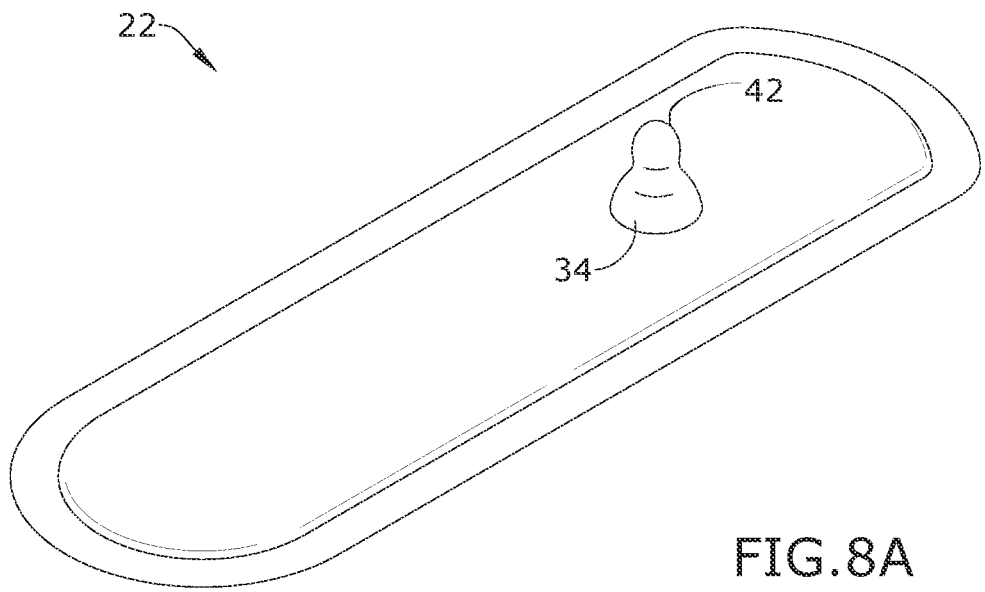
FIG. 8A is a bell shaped FIMD, pad front.
Figure 8B:
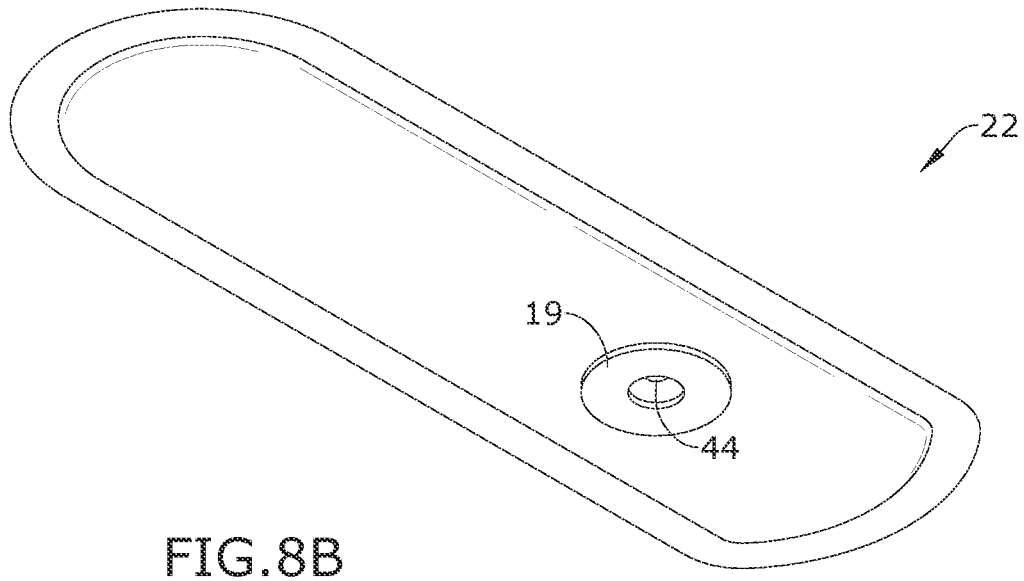
Figure 16A:
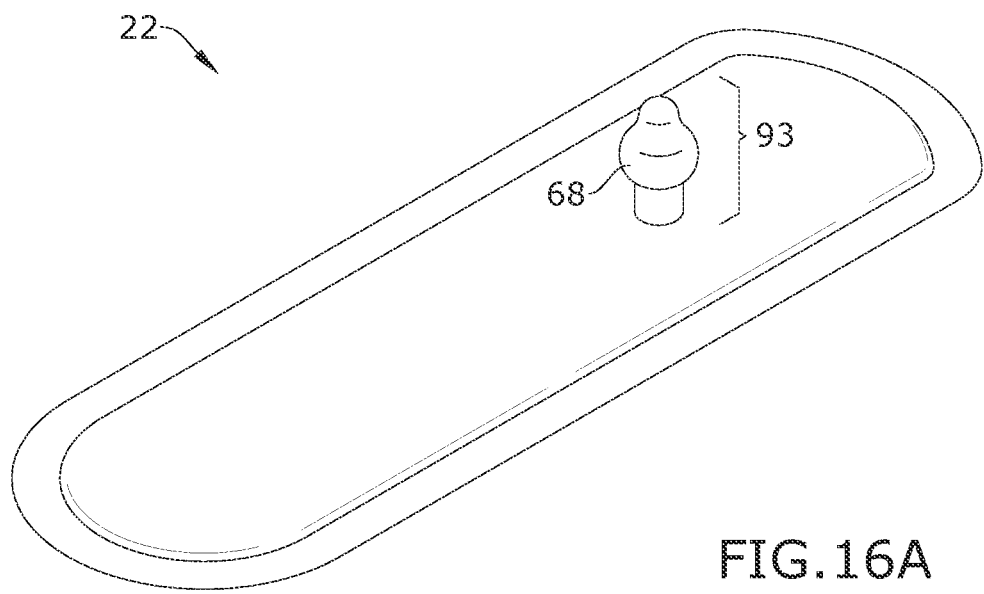
FIG. 16A is a front pad view of FIMD 93.
Figure 16B:
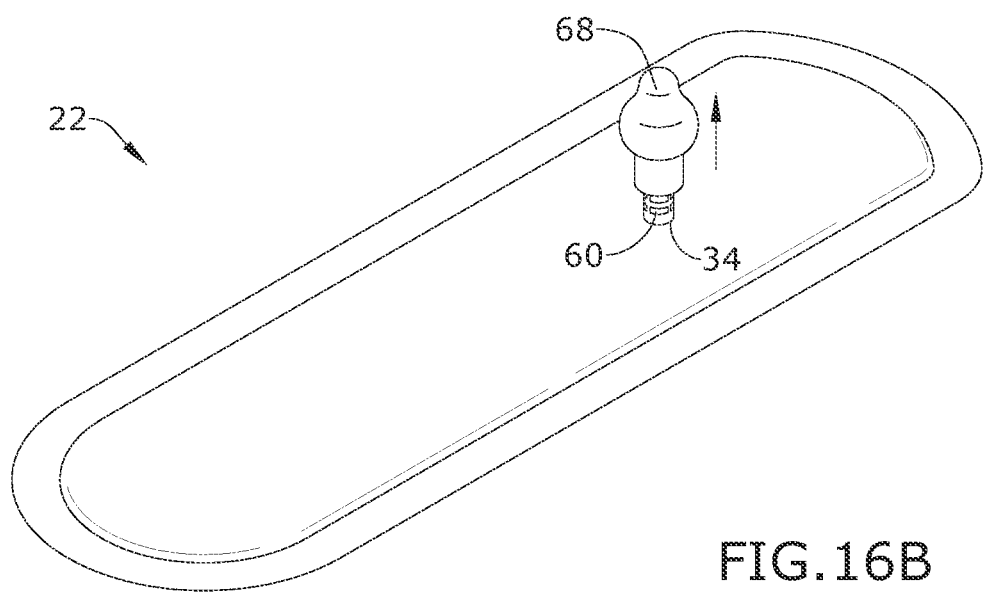
FIG. 16B is a front pad view of FIMD 93 showing a height adjustment.

FIGS. 7 and 8 show two types of Female Urinary Incontinence Management systems using FIMDs with a neoprene disc base. FIG. 8 shows protuberance 42 with integrated stiffener 44 front and back pad views of pad 22. The second base embodiment 9, the one-piece synthetic, is shown projecting from ideal opening 34, on the front side of the pad.14A. While 14B shows the pad back with base disk adhered, FIGS. 16A and 16B show FIMD 93 is adjustable for height on base post 60. FIG. 16 shows the third type of FUIMS disclosed in this patent.

Figures 17, 17A:
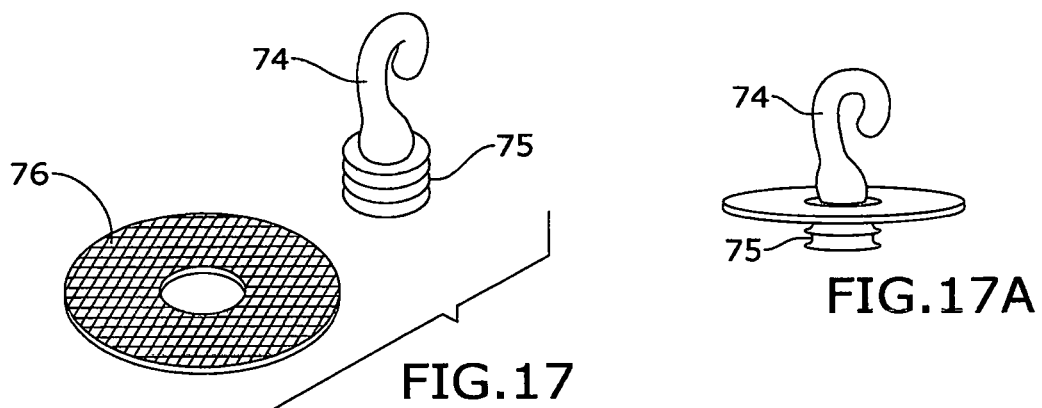
FIG. 17 is a conceptual perspective of BLUETOOTH components.
FIG. 17A is a conceptual illustration of the adjustable base.
Figure 18A:
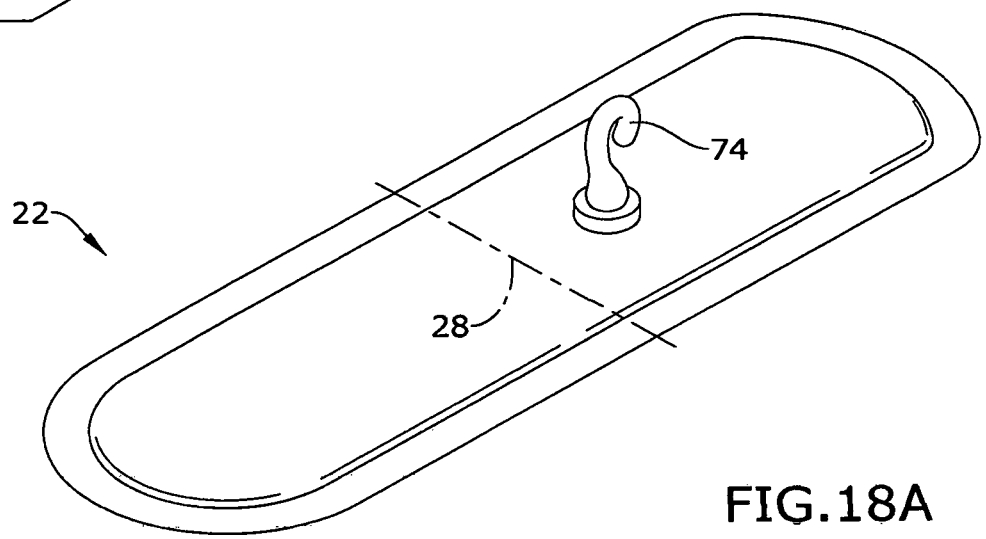
FIG. 18A is a conceptual illustration of BLUETOOTH FIMD, placement pad front.
Figure 18B:
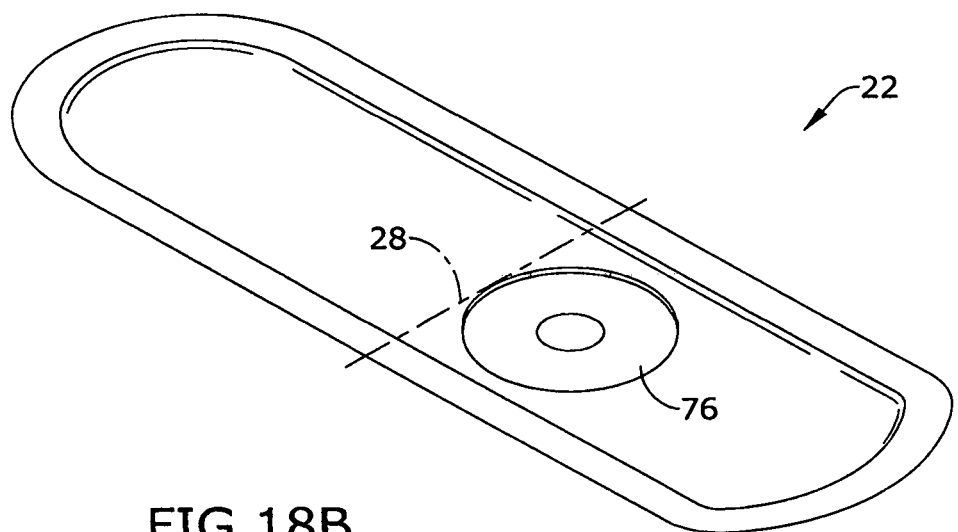
FIG. 18B is a conceptual Back pad view of the BLUETOOTH FIMD.

FIGS. 17 and 18 are conceptual drags of a BLUETOOTH enabled FIMD. The medical grade silicone elastomer device 74 has an abraded 2-inch disc 76 with an opening just large enough to fit snugly on its three tiered adjustable base 75. Because of the extra heaviness of the device, a pad opening is cut closer to medial line 28. The front lobe of the device could contain a biomorphic piezo disk or strip that is BLUETOOTH activated to vibrate, serving to stimulate the clitoris once pad 22 is worn.

Figure 19A:
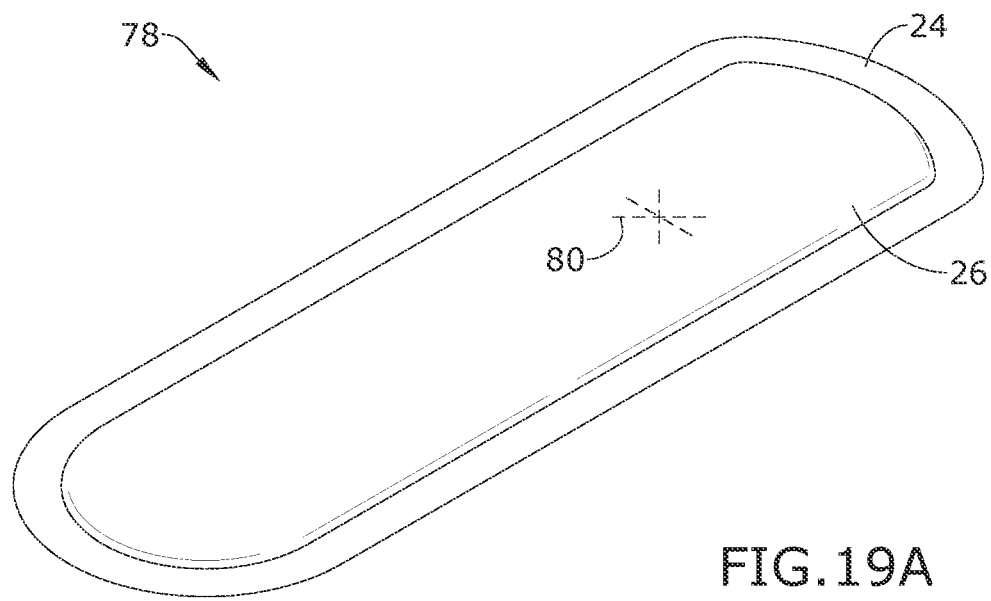
FIG. 19A is conceptual front view of a pad showing a perforated opening for an FIMD in a mass-produced pad.
Figure 19B:
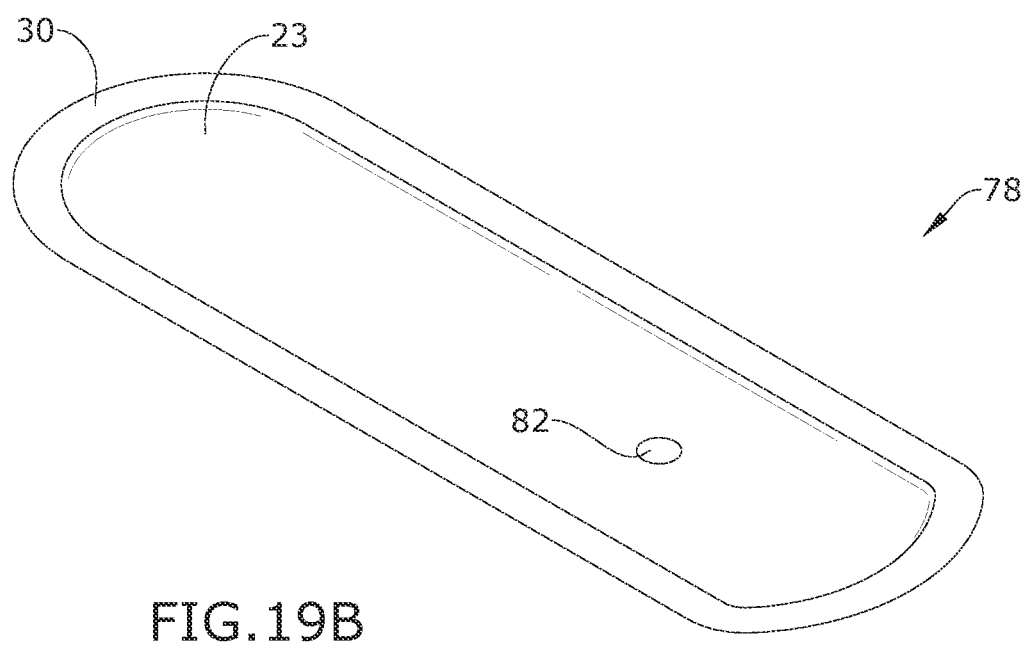
FIG. 19B is the back pad view showing a factory designation which corresponds to the perforated opening.
Figure 19C:
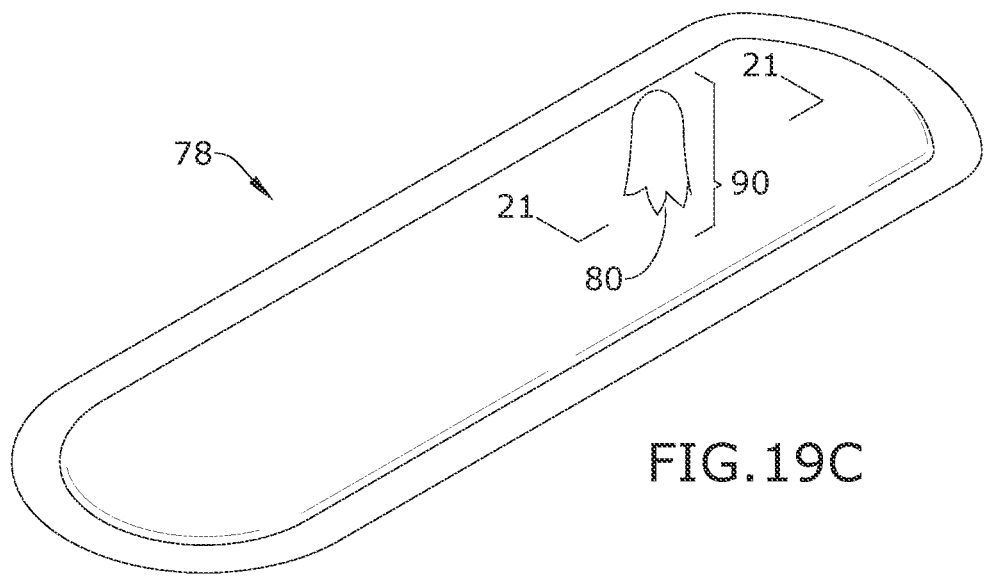
FIG. 19C is the FIMD through the pad back, projecting through the perforated opening.

FIG. 19A is a conceptual drawing of a mass-produced pad 78, with a perforated factory opening 80, in the pad front, and designation for insertion 82, on the pad back 23. The FIMD protuberance is shown tearing through 80. 21 is an optimum area for placement of an opening: 1 inch from the pad top, in the top ⅓ of the pad 78, along the medial lengthwise line.

Figure 20:
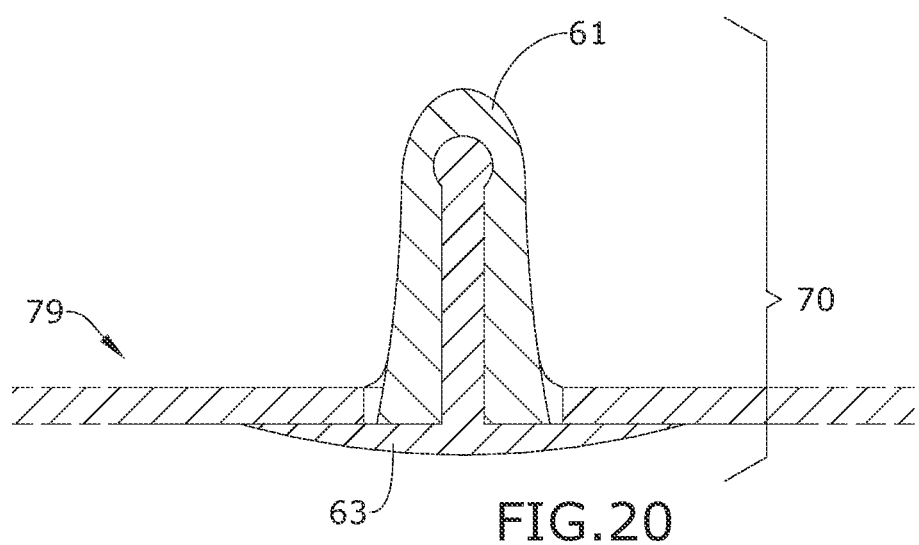
FIG. 20 is a conceptual cross-sectional view of a single use, manufactured pad with an embedded FIMD.

FIG. 20 is a conceptual cross section of a mass-produced pad with a factory embedded device 70, pad 79. The convex disc base 63 is part of a single unit synthetic insert which both anchors and stabilizes the FIMD, as it rests just under the top layer of the pad and above the bottom layer (not shown). The viscoelastic covering over the flared end of the insert is 61.

Figure 21:
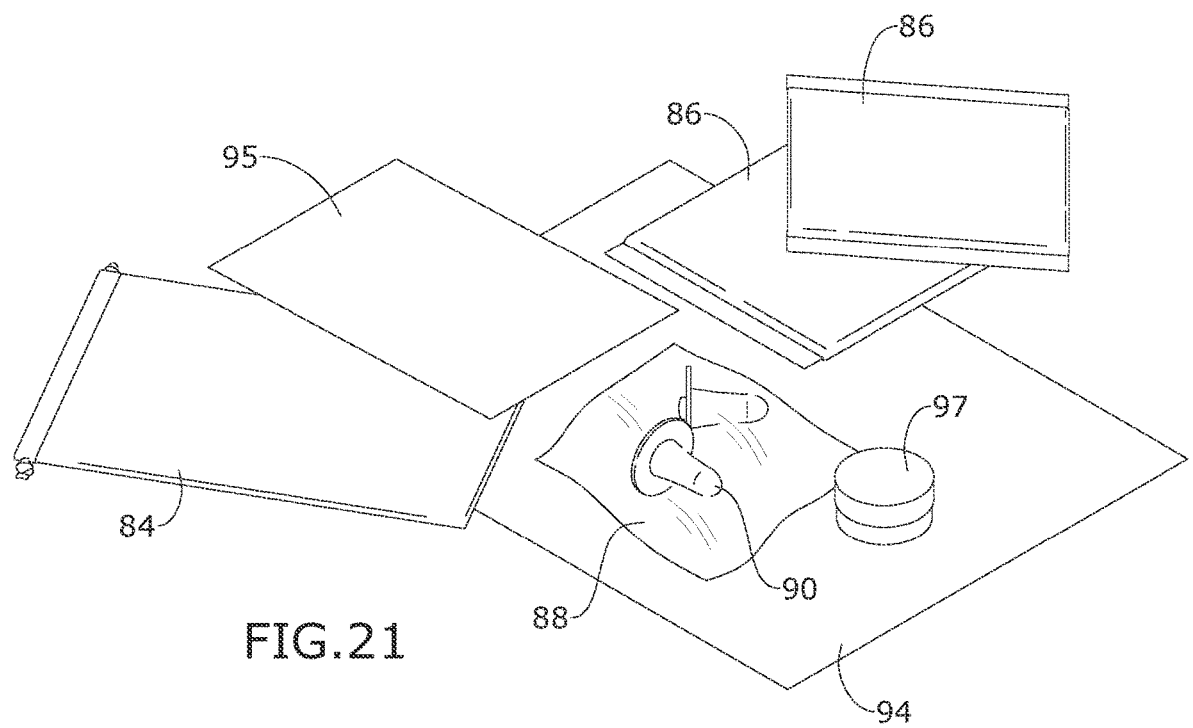
FIG. 21 is a perspective of kit parts.

FIG. 21 is of a promotional kit containing: 2 pads with pre-cut openings; two packaged FIMDs 88; a sanitizing tin 97; a reorder form 95; directions 94; carrying pouch 84. The FIMDs are viscoelastic protuberances with implanted stiffeners, PVC free FIMD s 90.

Figure 22A:
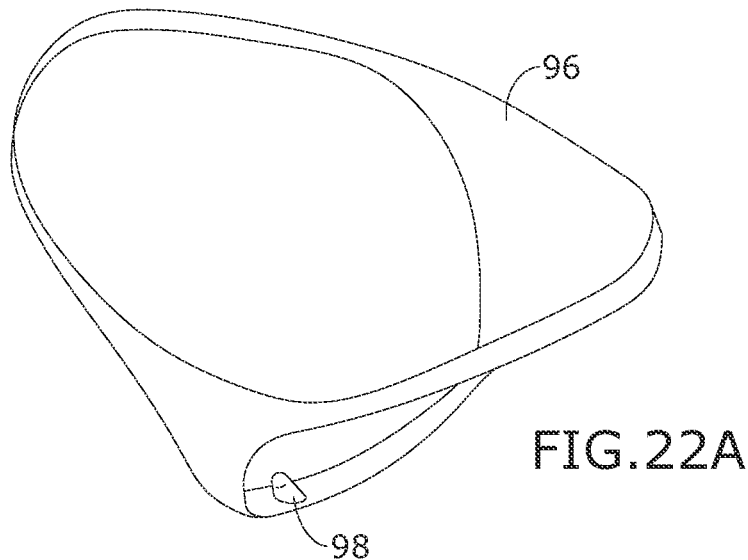
FIG. 22A is a conceptual view of a twin paneled (front and back) thong with a permanently embedded FIMD, which is reusable.

FIG. 22A shows a conceptual drawing of a porous twin paneled (equal front and back) thong 96, with a permanently embedded FIMD 98. The device might be fin shaped to deflect fluid, and made of denser material, than the protuberances in this patent—the user may need to use lubricant.

Figure 22B:
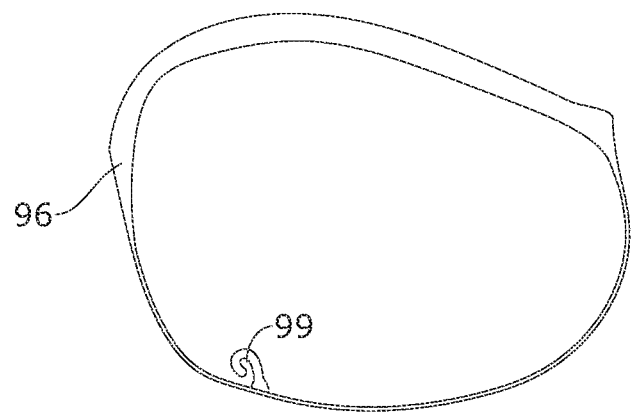
FIG. 22B is a conceptual BLUETOOTH enabled device that can be fitted onto a thong.

FIG. 22B is a conceptual drawing of a thong 96, with a removable BLUETOOTH enabled FIMD 99.

This patent discloses the fabrication of 4 types of Female Incontinence Management Devices (FIMD), using 4 distinct viscoelastic protuberances. Two of these protuberances are bonded to a neoprene disc base to create two types of Female Incontinent Management Devices (FIMD). Each can be pulled through the back of the pad through a specific opening to create a Female Urinary incontinence Management System (FUIMS). Two other protuberances are screwed onto the base post of a one piece synthetic where it projects from the pad front. These are the remaining two types of FIMDs disclosed in this patent. Each of their union with a pad forms a FUIMS.

What is claimed is:

1. A female incontinent management device comprising a soft and pliable re-useable protuberance with a top surface and a bottom surface, wherein the bottom surface of the protuberance is affixed to a neoprene disc base; wherein the top surface of the protuberance is configured to project into a wearer's clitoral-urethral meatus space between the wearer's Labia Majora and Labia Minora, the base of the wearer's clitoris, and the wearer's urethral meatus, and further wherein the top surface of the protuberance is configured to project onto, freely contact, apply, and maintain pain-free frictional pressure to the wearer's clitoris to ameliorate an urge to urinate by activating reflexive contraction of the bulbocavernosus and the ischiocavernosus muscles to close the wearer's external and internal urethral sphincters.

2. The female incontinent management device of claim 1, wherein the external diameter of the neoprene disc measures 2 inches or less.

3. The female incontinent management device of claim 1, wherein the neoprene disc has a center opening of ⅜ of an inch or less.

4. The female incontinent management device of claim 1, wherein the neoprene disc has a top abraded surface.

5. The female incontinent management device of claim 1, wherein the protuberance is viscoelastic foam.

6. The female incontinent management device of claim 1, wherein the top surface of the protuberance has a lesser diameter than the bottom surface of the protuberance.

7. The female incontinent management device of claim 1, wherein the protuberance is as high as 1¼ inches.

8. The female incontinent management device of claim 1, wherein the protuberance has an integrated stiffener.

9. The female incontinent management device of claim 1, wherein a stiffener is inserted into the protuberance.

10. The female incontinent management device of claim 1, wherein the protuberance has a factory-made opening.

11. A Female Urinary Incontinence Management System (FUIMS) comprising:
a female incontinent management device comprising a soft and pliable re-useable protuberance with a top surface and a bottom surface, wherein the top surface of the protuberance is configured to project into a wearer's clitoral-urethral meatus space between the wearer's Labia Majora and Labia Minora, the base of the wearer's clitoris, and the wearer's urethral meatus;
a neoprene disc base affixed to the bottom surface of the protuberance;
wherein the female incontinent management device is inserted into a sanitary napkin pad to form the Female Urinary Incontinence Management System; and further wherein the top surface of the protuberance is configured to project onto, freely contact, apply, and maintain pain-free frictional pressure to the wearer's clitoris to ameliorate an urge to urinate by activating reflexive contraction of the bulbocavernosus and the ischiocavernosus muscles to close the wearer's external and internal urethral sphincters.

12. The Female Urinary Incontinence Management System of claim 11, wherein the top surface of the female incontinent management device is pulled completely through the pad back.

13. The Female Urinary Incontinence Management System of claim 11, wherein the protuberance can be adjusted for height.

14. The Female Urinary Incontinence Management System of claim 11, wherein the sanitary napkin pad has an area for an opening: at least 1 inch from a pad top, in a top ⅓ of the pad, along a medial lengthwise line.

15. The Female Urinary Incontinence Management System of claim 14, wherein the opening can be factory replicated.

16. The Female Urinary Incontinence Management System of claim 11, wherein the sanitary napkin pad is mass produced with a positioned and embedded female incontinent management device.

17. The Female Urinary Incontinence Management System of claim 11 wherein, a nylon thong has an embedded female incontinent management device.

18. A kit containing a Female Urinary Incontinence Management System, the kit comprising:
at least one female incontinent management device comprising a soft and pliable re-useable protuberance with a top surface and a bottom surface, wherein the top surface of the protuberance is configured to project into a wearer's clitoral-urethral meatus space between the wearer's Labia Majora and Labia Minora, the base of the wearer's clitoris, and the wearer's urethral meatus;
a neoprene disc base affixed to the bottom surface of the protuberance;
at least one sanitary napkin pad with pre-cut opening, directions for use, and a carrying pouch, wherein the female incontinent management device is inserted into the sanitary napkin pad to form the Female Urinary Incontinence Management System; and further wherein the top surface of the protuberance is configured to project onto, freely contact, apply, and maintain pain-free frictional pressure to the wearer's clitoris to ameliorate an urge to urinate by activating reflexive contraction of the bulbocavernosus and the ischiocavernosus muscles to close the wearer's external and internal urethral sphincters.

19. A female incontinent management device comprising a soft and pliable re-useable protuberance with a top surface and a bottom surface, wherein the bottom surface of the protuberance twisted onto a post of a one-piece synthetic base, wherein the top surface of the protuberance is configured to project into a wearer's clitoral-urethral meatus space between the wearer's Labia Majora and Labia Minora, the base of the wearer's clitoris and urethral meatus, and further wherein the top surface of the protuberance is configured to project onto, freely contact, and apply, and maintain pain-free frictional pressure to the wearer's clitoris to ameliorate an urge to urinate by activating reflexive contraction of the bulbocavernosus and the ischiocavernosus muscles to close the wearer's external and internal urethral sphincters.

20. A Female Urinary Incontinence Management System (FUIMS) comprising:
a female incontinent management device comprising a soft and pliable re-useable protuberance with a top surface and a bottom surface, wherein the top surface of the protuberance is configured to project into a wearer's clitoral-urethral meatus space between the wearer's Labia Majora and Labia Minora, the base of the wearer's clitoris, and the wearer's urethral meatus;
a one-piece synthetic base with a post, wherein the bottom surface of the protuberance is twisted onto a post;
wherein the female incontinent management device is inserted into a sanitary napkin pad to form the Female Urinary Incontinence Management System; and further wherein the top surface of the protuberance is configured to project onto, freely contact, and apply, and maintain pain-free frictional pressure to the wearer's clitoris to ameliorate an urge to urinate by activating reflexive contraction of the bulbocavernosus and the ischiocavernosus muscles to close the wearer's external and internal urethral sphincters.

* * * * *